United States Patent [19]

Cumming et al.

[11] Patent Number: 4,642,229
[45] Date of Patent: Feb. 10, 1987

[54] BONE-SEEKING COMPLEXES OF TECHNETIUM-99M

[75] Inventors: Stephen A. Cumming, High Wycombe; James D. Kelly, Amersham, both of England

[73] Assignee: Amersham International plc, Buckinghamshire, England

[21] Appl. No.: 600,408

[22] Filed: Apr. 16, 1984

[30] Foreign Application Priority Data

Apr. 18, 1983 [GB] United Kingdom ............... 8310438

[51] Int. Cl.[4] ................. A61K 43/00; A61K 49/00; A61K 49/02
[52] U.S. Cl. ..................................... 424/1.1; 424/9; 534/14; 260/502.4 P
[58] Field of Search ................... 424/1.1, 9; 260/502.4 P; 534/14

[56] References Cited

U.S. PATENT DOCUMENTS

| | | | |
|---|---|---|---|
| 3,983,227 | 9/1976 | Tofe et al. | 424/1.1 |
| 4,088,747 | 5/1978 | Hunt et al. | 424/1.1 |
| 4,187,284 | 2/1980 | Rollestone et al. | 424/1.1 |
| 4,387,087 | 6/1983 | Deutsch et al. | 424/1.1 |
| 4,515,766 | 5/1985 | Castronovo et al. | 424/1.1 |

*Primary Examiner*—Christine M. Nucker
*Attorney, Agent, or Firm*—Wenderoth, Lind & Ponack

[57] ABSTRACT

A bone-seeking, Technetium-99m-ethylene glycol-1,2-bisphosphonate complex has been found to be useful as a bone-scanning agent. The complex, which is prepared by adding Technetium-99m, as an aqueous solution of pertechnetate, to a composition comprising a mixture of ethylene glycol-1,2-bisphosphonic acid or a non-toxic salt thereof with a reducing agent for pertechnetate, is taken up rapidly in bone to give scans of high definition and compares favorably in this and other respects to other bone-scanning agents.

6 Claims, No Drawings

BONE-SEEKING COMPLEXES OF TECHNETIUM-99M

In April 1971, G. Subramanian and J. G. McAfee described (Radiology, 99, 192–6) a bone scanning agent prepared by reducing pertchnetate TcO4− with stannous chloride in the presence of tripolyphosphate. The resulting labelled complex gave good skeletal uptake but suffered from several disadvantages, the most important of which were a 24-hour delay between injection and scanning (so that high levels of radioactivity were required in order to obtain adequate instrument response), and the instability of the tripolyphosphate with respect to hydrolysis.

An intensive search in the 1970's for better phosphate- and phosphonate-based bone scanning agents has resulted in a large number of publications and several commercial products. The most widely used compound is methylene diphosphonate (MDP), the complex of which with tin and Technetium-99m is the subject of U.S. Pat. No. 4,032,625. Recent introductions to the market have included hydroxymethylene diphosphonate (HDP), which is the subject of European patent application 7676; and 1,1-diphosphonopropane-2,3-dicarboxylic acid (DPD), which is described in German O.S. No. 2755874.

A successful bone scanning agent requires inter alia high and rapid uptake of the agent in bone with rapid excretion from the blood and soft tissues such as muscle of that part of the agent not taken up in the bone. In order to achieve scans of high definition, current bone agents normally require an interval of two hours or even more between injection of the agent into the patient and performance of the scan. (The word "scan" is here taken to include gamma-camera imaging techniques.) Even small reductions of the interval between injection and scanning are highly desirable and could lead to worthwile increases in convenience to patient and physician and in the efficiency of the running of nuclear medicine units.

The present invention arises from our discovery that ethylene glycol-1,2-bisphosphonic acid shows high and rapid uptake in bone without any apparent concomitant disadvantage. In one aspect the invention provides a composition for the preparation of a bonescanning agent comprising a mixture of ethylene glycol-1,2-bisphosphonic acid or a non-toxic salt thereof together with a reducing agent for pertechnetate. On addition of an aqueous solution of pertechnetate, for example the isotonic saline eluent from a technetium-99m generator, the technetium is reduced from the 7+ to a lower valency in which it forms a complex with the ethylene glycol-1,2-bisphosphonic acid, which complex forms another aspect of this invention. The exact nature of the complex formed is not known; the reducing agent may possibly also form part of the complex. After shaking or standing for a short period to ensure complete reduction and complex formation, the liquid is ready for injection.

Ethylene glycol-1,2-bisphosphonic acid has the formula

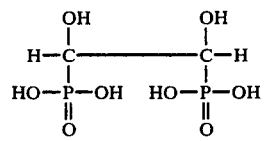

It is a known compound (Chem. Abs. Regn. No. 84351-11-1), described by Mikroyannidis et al in Phosphorus and Sulfur, 1982, 13, 279–89. It may be obtained by acid catalyzed hydrolysis of 1,2-dihydroxy-1,2-bis(-dialkoxyphosphonyl)ethanes; or by hydrogenation of 1,2-dihydroxy-1,2-bis(dibenzyloxyphosphonyl)ethane in the presence of palladium on carbon. The compound has two asymmetric carbon atoms and is accordingly optically active. This invention envisages the use of either the d- or the l-form, or the meso form or a mixture of any or all of these, since it is quite likely that one form will prove to have better biological properties than the others. Instead of the bisphosphonic acid, there may be used a non-toxic salt such as the sodium salt.

Known reducing agents for pertechnetate include tin (2+), iron (2+), and chromium (2+) salts and tin metal. Tin, as the metal or more particularly as a stannous salt, is the most widely used reducing agent for this purpose, and is preferred for use in this invention. When the reducing agent is in the form of a salt, the use of the bisphosphonic acid in a molar excess over the salt helps to stabilise the composition.

The composition may be prepared simply by mixing an aqueous solution of the ethylene glycol-1,2-bisphosphonic acid or salt with a solution of the reducing agent. If the reducing agent is stannous chloride, it may be used in solution in ethanol to minimise problems of hydrolysis. The pH of the mixture may be adjusted, preferably to a value in the range 3–9, preferably 4–8. If desired, the mixture may be dispensed into sealed vials, freeze-dried if not already sterile, and, finally sterilized.

An inert bulking agent may if desired be added to assist in dispensing small amounts into individual vials. Other known additives may also be included, particularly stabilising agents such as nitrate or nitrite, or para-aminobenzoic acid.

A preferred formulation includes from 0.1 to 1.0 mg of stannous chloride or other reducing agent with from 1.0 to 50 mg of ethylene glycol-1,2-bisphosphonic acid or its sodium salt in a vial for activation by from 1 to 15 ml of saline eluate from a technetium-99m generator.

The following Example shows the unexpectedly good results achieved by compositions according to this invention.

EXAMPLE

In all experiments, the stated weight of ethylene glycol-1,2-bisphosphonic acid in solution in isotonic saline was adjusted to the required pH and was mixed with an ethanolic solution of 0.3 mg of stannous chloride. In one case 2 mg of the sodium para-aminobenzoate were added as a stabilizer. To the mixture was added 1 ml of generator eluent containing 12 mCi of pertechnetate in isotonic saline. The mixture was held in a nitrogen purged vial for 15 minutes, and aliquots were then injected into male rats. These were sacrificed and dissected at 15 minutes or 2 hours after injection. The biodistribution results of one experiment are set out in Table 1 below, each figure being the average from 3 rats. Also included in this table are representative results obtained using 4 commercially available bone-scanning kits. The following abbreviations are used:-

HDP—Hydroxymethylene diphosphonate (Kit ex Procter & Gamble)
MDP—Methylene diphosphonate (Kit ex Amersham International)
DPD—1,1-diphosphonopropane-2,3-dicarboxylic acid (Kit ex Hoechst)
P-MDP—MDP stabilised with para-aminobenzoic acid (Kit ex Amersham International)
DPEG—Ethylene glycol-1,2-bisphosphonic acid (composition of this example).

TABLE 1

BIODISTRIBUTION IN RATS

|  |  | HDP | MDP | DPD | P-MDP | DPEG pH 5.0 10 mg/vial |
|---|---|---|---|---|---|---|
| % Bone | 15 m | 38.7 | 35.1 | 33.3 | 37.4 | 45.3 |
|  | 2 hr | 50.3 | 42.7 | 49.9 | 44.7 | 52.0 |
| % Bladder & urine | 15 m | 35.4 | 32.5 | 30.1 | 34.1 | 30.1 |
|  | 2 hr | 43.3 | 51.4 | 45.3 | 47.9 | 45.2 |
| Bone/ muscle | 15 m | 44 | 41 | 30 | 48 | 54 |
|  | 2 hr | 657 | 390 | 822 | 594 | 799 |
| Bone/ blood | 15 m | 12 | 12 | 5 | 13 | 12 |
|  | 2 hr | 318 | 186 | 195 | 278 | 206 |
| Bone/ liver & spleen | 15 m | 21 | 37 | 8 | 52 | 27 |
|  | 2 hr | 31 | 139 | 20 | 244 | 47 |

As can be seen from the column headed "DPEG", the % bone uptake was higher at both 15 minutes and 2 hours than for any of the commercial preparations. Also the bone/muscle ratio (which is more important for good quality skeletal imaging than the bone/blood ratio) was higher at 15 minutes than for any of the commercial preparations. The results indicate some slight unwanted liver uptake, but this is a phenomenon often encountered and eliminated by careful formulation. It should be noted that the results are for a composition of this invention which has not in any way been refined or optimised, in marked contrast to the four commercial compositions whose results are included for comparison. It is likely that optimised compositions according to the present invention will give more dramatic improvements.

Table 2 gives biodistribution results in rats of five different compositions according to the invention. The pH was varied between 4 and 7.9. The amount of DPEG used was 5 mg or 10 mg per vial. In one case a stabiliser was included.

TABLE 2

BIODISTRIBUTION IN RATS

|  |  | DPEG pH 5.0 5 mg/vial | DPEG pH 4.0 5 mg/vial | DPEG pH 5.0 10 mg/vial | DPEG pH 7.9 10 mg/vial | Stabilised DPEG pH 5.0 5 mg/vial |
|---|---|---|---|---|---|---|
| % Bone | 15 m | 45 | 35 | 45 | 32 | 40 |
|  | 2 hrs | 55 | 48 | 52 | 46 | 51 |
| % Bladder & urine | 15 m | 31 | 30 | 30 | 20 | 30 |
|  | 2 hrs | 45 | 48 | 45 | 45 | 42 |
| Bone/ muscle | 15 m | 45 | 36 | 54 | 23 | 56 |
|  | 2 hrs | 481 | 431 | 799 | 573 | 678 |
| Bone/ blood | 15 m | 11 | 7 | 12 | 6 | 13 |
|  | 2 hrs | 132 | 103 | 206 | 193 | 237 |
| Bone/ liver & spleen | 15 m | 30 | 7 | 27 | 17 | 28 |
|  | 2 hrs | 64 | 11 | 47 | 37 | 51 |

Table 3 gives biodistribution results in rats of compositions containing DPEG and two structurally similar compounds (10 mg/vial at pH 6.5). Each figure is the average of results obtained from two male rats sacrificed two hours after injection.

TABLE 3

BIODISTRIBUTION IN RATS

|  | Ethane-1,2-bisphosphonic acid | 1-Hydroxyethane-1,2-bisphosphonic acid | Ethylene glycol-1,2-bisphosphonic acid |
|---|---|---|---|
| % Bone | 40 | 43 | 48 |
| % Bladder & urine | 55 | 48 | 41 |
| Bone/ muscle | 200 | 293 | 820 |
| Bone/ blood | 36 | 41 | 223 |
| Bone/liver & spleen | 20 | 34 | 86 |

The figures in the right-hand column represent a composition according to this invention. They are surprisingly superior to the figures obtained using the two structurally similar compounds. The % bone uptake at 2 hours is higher, and the bone/muscle, bone/blood and bone/liver & spleen ratios are all markedly greater.

It might be expected that DPEG would exhibit a toxicity similar to the known toxicities of the phosphonates used in commercially-available bone scanning agents. Results obtained from experiments on rats suggest that this is not the case and that DPEG is less toxic compared to other bone agents. This is surprising and the reason for this apparent anomaly is not known.

The present invention to currently being performed in clinical trials on humans. Initial results, using non-optimised formulations are satisfactory.

What is claimed is:

1. A composition for use in the preparation of a Technetium-99m bone scanning agent comprising a mixture of ethylene glycol-1,2-bisphosphonic acid or a non-toxic salt thereof together with a non-toxic reducing agent for pertechnetate ions.

2. The composition as claimed in claim 1, wherein the reducing agent is a non-toxic salt of tin (2+), iron (2+) or chromium (2+).

3. The composition as claimed in claim 2, wherein the reducing agent is a non-toxic stannous salt.

4. The composition as claimed in claim 2, wherein the ethylene glycol-1,2-bisphosphonic acid or non-toxic salt thereof is present in a molar excess over the reducing agent.

5. A bone-seeking composition comprising an aqueous solution of a complex of Technetium-99m and ethylene glycol-1,2-bisphosphonic acid.

6. A bone-seeking composition comprising an aqueous solution of a Technetium-99-m-tin-ethylene glycol-1,2,-bisphosphonate complex.

* * * * *